US009035083B2

(12) United States Patent
Montchamp et al.

(10) Patent No.: US 9,035,083 B2
(45) Date of Patent: May 19, 2015

(54) SYNTHESIS OF H-PHOSPHONATE INTERMEDIATES AND THEIR USE IN PREPARING THE HERBICIDE GLYPHOSATE

(71) Applicant: Texas Christian University, Fort Worth, TX (US)

(72) Inventors: Jean-Luc Montchamp, Fort Worth, TX (US); Henry C. Fisher, Fort Worth, TX (US)

(73) Assignee: Texas Christian University, Fort Worth, TX (US)

( * ) Notice: Subject to any disclaimer, the term of this patent is extended or adjusted under 35 U.S.C. 154(b) by 0 days.

(21) Appl. No.: 14/221,931

(22) Filed: Mar. 21, 2014

(65) Prior Publication Data

US 2014/0303394 A1    Oct. 9, 2014

Related U.S. Application Data

(60) Provisional application No. 61/808,942, filed on Apr. 5, 2013.

(51) Int. Cl.
*C07F 9/40* (2006.01)
*C07F 9/38* (2006.01)

(52) U.S. Cl.
CPC ............ *C07F 9/3808* (2013.01); *C07F 9/3813* (2013.01); *C07F 9/4006* (2013.01)

(58) Field of Classification Search
None
See application file for complete search history.

(56) References Cited

U.S. PATENT DOCUMENTS

| 3,799,758 A | 3/1974 | Franz |
| 3,954,848 A | 5/1976 | Franz |
| 4,237,065 A | 12/1980 | Ehrat |
| 5,208,000 A | 5/1993 | Yang et al. |

FOREIGN PATENT DOCUMENTS

CN     101550158 A    10/2009

OTHER PUBLICATIONS

Coudray, et al.; "New Access to H-phophonates via metal-catalyzed phophorous-oxygen bond formation;" Article; Jul. 13, 2007; 4 pages; Tetrahedron Letters 48; Science Direct; www.sciencedirect.com.
Rhodia Slide Presentation; Glyphosate Panel; May 2008; 11 pages; San Antonio, TX.
Jacek Stawinski, "Some Aspects of H-Phophonate Chemistry;" Article; pp. 377-434; Handbook of Organophosphorus Chemistry; R. Engle, Ed., Marcel Dekker; New York; 1992.
Stawinski et al.; "How to Get the Most Out of Two Phosphorus Chemistries, Studies of H-Phophonates"; Accounts of Chemical Research; vol. 35, No. 11; Article; 9 pages; copyright 2002 American Chemical Society.

*Primary Examiner* — Sun Jae Yoo
(74) *Attorney, Agent, or Firm* — Charles D. Gunter, Jr.

(57) ABSTRACT

The esterfication of hypophosphorous acid is followed by reaction with another molecule of alcohol under the action of a nickel catalyst to provide a green method for the preparation of H-phosphonate diesters. This method avoids the need for any stoichiometric chlorine unlike those based on phosphorous trichloride.

12 Claims, 2 Drawing Sheets

_US 9,035,083 B2_

SYNTHESIS OF H-PHOSPHONATE INTERMEDIATES AND THEIR USE IN PREPARING THE HERBICIDE GLYPHOSATE

CROSS REFERENCE TO RELATED APPLICATIONS

The present application claims priority from a provisional application Ser. No. 61/808,942, filed Apr. 5, 2013, entitled "Synthesis of H-Phosphonate Intermediates and Their Use in Preparing the Herbicide Glyphosate", by the same inventors.

BACKGROUND OF THE INVENTION

1. Field of the Invention

A process for the conversion of hypophosphorous acid ($H_3PO_2$, HPA) and alcohols into various H-phosphonate diesters $(RO)_2P(O)H$ completely avoiding $PCl_3$. Nickel chloride or nickel on silica catalyze the oxidative phosphorylation of alkyl phosphinates with various alcohols or water. The H-phosphonates so produced can be used in the preparation of various organophosphorous compounds including the industrially important herbicide glyphosate.

2. Description of the Prior Art

Organophosphorus compounds are very important compounds both economically and industrially. These compounds may be defined as compounds containing a phosphorus-carbon bond, although alkyl phosphate esters, which contain only phosphorus-oxygen (P—OR) bonds are the important exception to this definition. These compounds are used in numerous applications such as flame retardants, herbicides and pesticides, medicines and materials. One such class of compounds, the H-phosphonates are an important class of phosphorus-containing intermediates that are used in the production of one of the most prolific herbicide, glyphosate (N-phosphonomethylglycine). Glyphosate is sold commercially under the tradename Roundup® by Monsanto Company.

While the use of herbicides is not perfect, it would not be possible to sustain food production for the planet's population without them. Glyphosate has been widely used since its introduction in the 1970's and is considered to be "virtually ideal" due to its broad spectrum and low toxicity compared with other herbicides. Its use increased even more when Monsanto introduced glyphosate-resistant crops, enabling farmers to kill weeds without killing their crops. While herbicides are here to stay, more environmentally friendly and energy efficient production are essential for sustainable processes. Today, novel methods are needed to better employ feedstocks for organophosphorus synthesis and these new methods need to address many issues such as increased safety, efficiency and sustainability, lower energy consumption, and less waste product formation, to name a few.

Currently, almost all organophosphorus compounds are synthesized industrially from $PCl_3$ which itself is prepared from the chlorination of elemental phosphorous ($P_4$). The production of $PCl_3$ is hazardous and environmentally problematic. Furthermore, $PCl_3$ is a highly reactive compound and has been implicated in major industrial accidents. Additionally, the production of chlorine itself is even more dangerous and energy demanding as it is made via electrolysis. Some outdated chlorine plants are even responsible for a significant portion of preventable mercury pollution. The transformation of $PCl_3$ into other organophosphorus compounds is never atom-economical and always results in the formation of wasteful HCl. Approximately half of all $PCl_3$ produced globally goes into the production of the herbicide glyphosate.

Because of phosphorus trichloride's obvious drawbacks, significant research efforts have been devoted to bypass its use. A popular proposal relies on the so-called "$P_4$-activation" pathway. Since $P_4$ is already the precursor to all other organophosphorus compounds, as well as most inorganic phosphorus reagents, this appears to be a logical strategy. However, a fundamental problem with $P_4$-activation is that not all phosphorus atoms can be used (the only exception being its conversion to $PCl_3$). This is due to the fact that the phosphorus tetrahedron is broken, the reactivity of the P—P bonds decreases. Furthermore, $P_4$ is toxic and pyrophoric, and thereby better employed in-situ. It is also insoluble in standard organic solvents (carbon disulfide is not a convenient solvent because of its extremely low flash point and autoignition temperatures).

Two other pathways that have received significant attention to bypass $PCl_3$ in the preparation of organophosphorus compounds are: a) the use of $PH_3$, and b) the use of $P_{red}$. Both have found some support in the literature and in practice. However, $PH_3$ is a highly toxic and pyrophoric gas requiring very careful handling, and $P_{red}$ uses "superbasic" conditions (aqueous KOH/DMSO, the Trofimov-Gusarova reaction) for functionalization. Additionally, the latter $P_{red}$-based approach requires heating white phosphorus to prepare $P_{red}$, and it does not solve the issue of phosphorus atom economy.

Approximately 350,000 metric tons of $PCl_3$ are produced annually and as stated, 50% of $PCl_3$ production goes solely into the production of glyphosate. It is expected that glyphosate usage will increase in the near future. Glyphosate is already nearly a \$1 billion product. Because of the economic importance of glyphosate, there has been significant research devoted to its production. Generally, glyphosate is made from either one of three general processes: $PCl_3$+formaldehyde+$HN(CH_2COOH)_2$ and then oxidative cleavage to glyphosate $(HO)_2P(O)CH_2NCH_2COOH$, or a similar process using phosphorous acid ($H_3PO_3$). Phosphorous acid is currently made from the hydrolysis of $PCl_3$ so 3HCl molecules are also formed. The third process, which is used in China, employs dialkyl H— phosphonates instead, but the current preparation of $(RO)_2P(O)H$ also produces 3HCl molecules from $PCl_3$. These processes are shown in FIG. 1.

What is needed is a chlorine free route for producing organophosphorus intermediates such as H-phosphonates which could then be used to produce useful industrial-scale products, such as glyphosate. The ability to prepare glyphosate from phosphinates in this way circumvents the use of chlorine and reduces the production of harmful by-products. Although there is growing consensus that using chlorine and $PCl_3$ should be minimized or avoided, the current method of production is unlikely to be easily changed due to the large scale of production and the complexity and costliness of changing large scale industrial processes. The present invention would represent a shift toward a more energy efficient, safer and environmentally friendlier production of glyphosate and is key to realigning the phosphorus economy away from $PCl_3$.

The present invention has as its object, therefore, to develop a route for the catalytic transformation of phosphinates into H-phosphonates without the use of the hazardous compound $PCl_3$, thereby enabling a more environmentally friendly synthetic route for the production of industrially important organophosphorus compounds, such as the herbicide glyphosate.

SUMMARY OF THE INVENTION

Phosphinate [$ROP(O)H_2$] is converted into H-phosphonate [$(RO)_2P(O)H$] using a suitable catalyst, such as a metal catalyst. Phosphinates are industrially prepared on large scale, directly from elemental phosphorus, and therefore do not require the intermediacy of chlorine $Cl_2$ and its derivative $PCl_3$. As has been discussed, H-phosphonates are important industrial intermediates normally prepared from the alcoholysis or hydrolysis of phosphorus trichloride ($PCl_3$), and used in numerous commercial applications, from flame-retardants, to extractants, to pesticides, etc. One of the most important industrial uses of H-phosphonates is in the manufacture of glyphosate (N-phosphonomethylglycine), the active ingredient in the number one selling herbicide Roundup® produced by Monsanto Company. However, phosphonates themselves do not contain chlorine. A method for bypassing chlorine entirely, would be environmentally and energetically desirable. Briefly stated, the present invention describes the conversion of phosphinate ROP(O)H$_2$ into H-phosphonate (RO)$_2$P(O)H(R=metal, H, alkyl, etc.) and the use of the intermediates thus prepared in the preparation of the industrially important organophosphorus compounds, particularly the industrially significant herbicide glyphosate.

In its preferred form, a method is shown for producing H-phosphonates circumventing the use of chlorine, the method comprising the steps of:

reacting hypophosphorous acid with an alcohol to produce a phosphinate and an excess of alcohol, or alternately reacting hypophosphorous acid with an excess of alkoxysilane to produce a phosphinate;

reacting the phosphinate in the presence of the excess alcohol with a metal catalyst to produce a H-phosphonate.

Preferably, the metal catalyst is selected from the group consisting of nickel, iron, manganese, copper and palladium compounds and nickel on silica and/or alumina. Most preferably, the catalyst is selected from among the metal catalysts NiCl$_2$ and Ni/SiO$_2$.

A method is also shown for using the H-phosphonate so produced in the production of the herbicide glyphosate. In the method for producing glyphosate, according to the teaching of the invention, a selected alkyl phosphinate is used as a starting material. The selected phosphinate is first converted to an H-phosphonate using excess alcohol in the presence of a metal catalyst. The H-phosphonate so produced is then converted to glyphosate using known techniques. In one form of the inventive method, the phosphinate is produced using hypophosphorous acid as the starting material. The phosphinate can also be produced industrially directly from elemental phosphorus without requiring the intermediary of chlorine.

Additional objects, features and advantages will be apparent in the written description which follows.

DETAILED DESCRIPTION OF THE INVENTION

The preferred version of the invention presented in the following written description and the various features and advantageous details thereof are explained more fully with reference to the non-limiting examples included and as detailed in the description which follows. Descriptions of well-known components and processes and manufacturing techniques are omitted so as to not unnecessarily obscure the principal features of the invention as described herein. The examples used in the description which follows are intended merely to facilitate an understanding of ways in which the invention may be practiced and to further enable those skilled in the art to practice the invention. Accordingly, the examples should not be construed as limiting the scope of the claimed invention.

Brief Description of the Experimental Work

The present invention comprises a critical bridge between phosphine-based chemistry and the established PCl$_3$ route for preparing organophosphorus intermediates, such as in the preparation of H-phosphonate diesters, (RO)$_2$P(O)H. This is an important distinction because the synthesis of phosphinates [ROP(O)H$_2$] does not rely on PCl$_3$, instead it can be industrially prepared from elemental phosphorus. In its preferred form, the present invention involves the transformation of phosphinate into H-phosphonate [(RO)$_2$P(O)H] and its application to the production of glyphosate. With this novel pathway, the ability to prepare glyphosate from phosphinates circumvents the use of any chlorine, and reduces the amount of by-products (especially hydrochloric acid, HCl).

Simply stated, phosphinate can be converted into H-phosphonate using a suitable catalyst, such as a metal catalyst. In one preferred method of practicing the invention, hypophosphorous acid (H$_3$PO$_2$) is first converted to an alkyl phosphinate, ROP(O)H$_2$, using an alcohol and then to (RO)$_2$P(O)H using the excess alcohol in the presence of a catalyst. The metal catalyst can be, for example, a metal catalyst selected from the group consisting of nickel, copper and palladium compounds and nickel on alumina. As has previously been described, normally, (RO)$_2$P(O)H is prepared from the reaction PCl$_3$+2 ROH+H$_2$O=(RO)$_2$P(O)H+3HCl.

Figure 1:
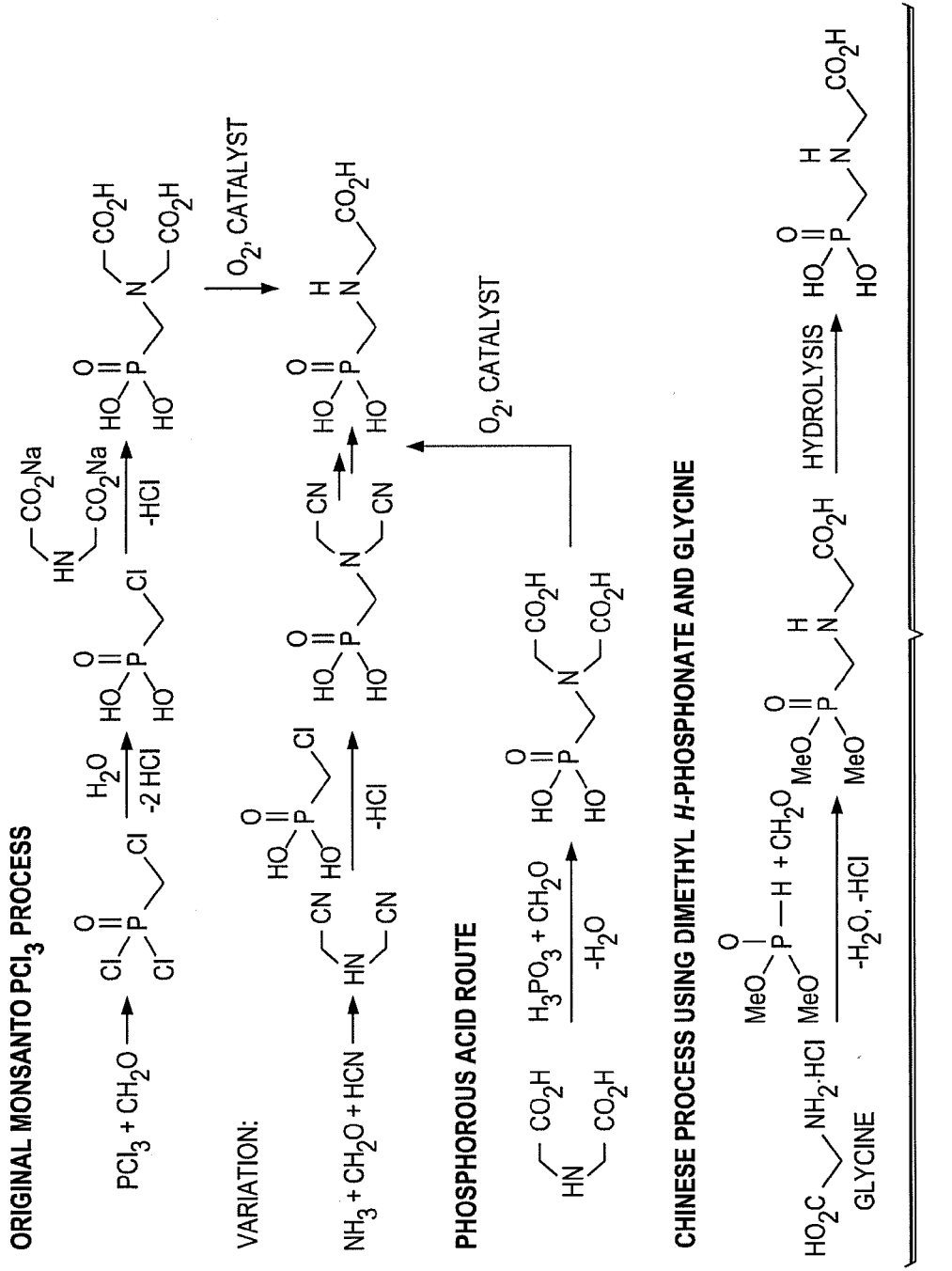
FIG. 1 is a flow diagram of existing processes used to produce glyphosate.
Figure 2:
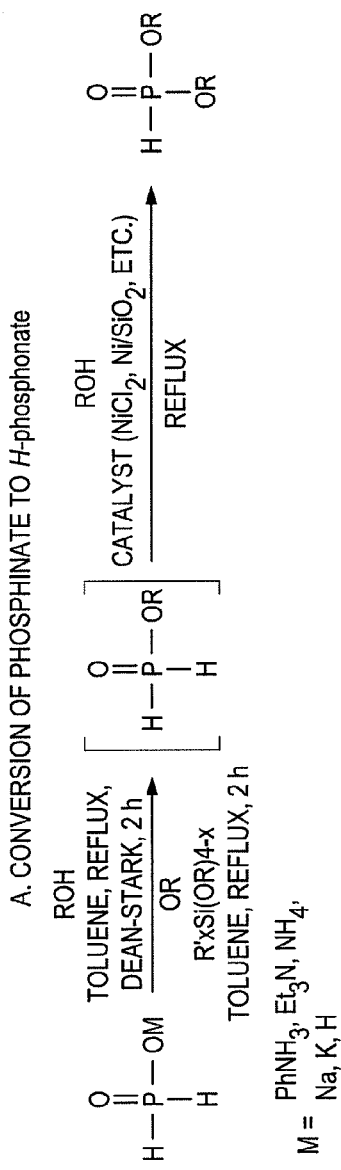
FIG. 2 is a chemical reaction showing the conversion of phosphinate to H-phosphonate.
Figure 3:
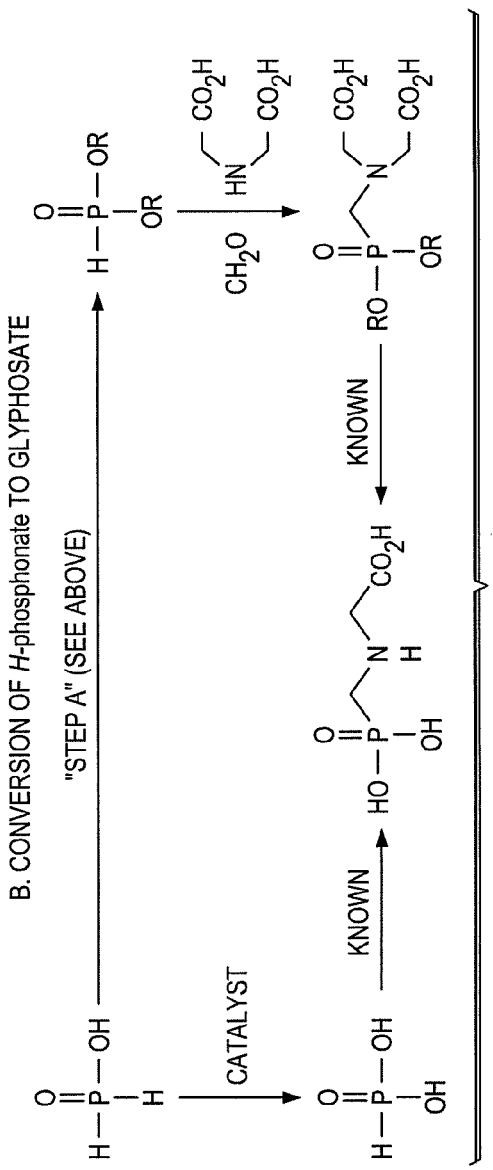
FIG. 3 is a chemical reaction showing the conversion of H-phosphonate to Glyphosate.

The steps in the method of the invention are shown schematically in FIGS. 2 and 3 of the drawings.

EXAMPLE 1

Preparation of Alkyl H-Phosphonates by Dean-Stark Esterification Followed by Metal-Catalyzed Oxidation Aqueous hypophosphorous acid (50 wt. %, 10 mmol) was weighed into a round bottom flask and concentrated under reduced pressure for 15 minutes at room temperature. Butanol (30 mmol) and toluene (to 0.5 M) were added to the reaction vessel, and the solution was heated to reflux for 2 hours under nitrogen atmosphere. During this period, water was collected in a Dean-Stark trap filled with excess toluene. $^{31}$P-NMR analysis of the cooled solution showed near quantitative formation of butyl phosphinate. The Dean-Stark trap was removed and Ni/SiO$_2$ (65 wt. %, 0.5 mmol) was added. The mixture was refluxed at good agitation for a period of 16 to 18 hours. $^{31}$P-NMR analysis of the formed H-phosphonate showed >90% purity.

EXAMPLE 2

Preparation of Alkyl H-Phosphonate Using Alkoxysilane Esterification Followed by Metal-Catalyzed Oxidation Aqueous hypophosphorous acid (50 wt. %, 10 mmol) was concentrated under reduced pressure for 15 minutes at room temperature. Dimethyldiethoxysilane (20 mmol) and toluene (up to 0.5M) was added to the reaction vessel, and the solution was heated to reflux for 2 hours under nitrogen atmosphere. NMR analysis showed quantitative formation of ethyl phosphinate. After cooling, ethanol (30 mmol) and Ni/SiO$_2$ (65 wt. %, 0.5 mmol) was added, and the mixture was refluxed for 30 hours. $^{31}$P-NMR analysis showed >90% purity of the formed H-phosphonate.

EXAMPLE 3

Preparation of Glyphosate Using Alkyl-H-Phosphonate

Methanol was added to iminodiacetic acid (15 mmol), paraformaldehyde (23 mmol) and triethylamine (30 mmol).

The mixture was refluxed for 2 hours, and upon completion was cooled and concentrated under reduced pressure to remove the excess methanol and triethylamine. Crude H-phosphonate solution as prepared in either Example 1 or Example 2 was added to imine intermediate, and refluxed for another 2 hours. $^{31}$P-NMR analysis showed >90% completion of the reaction. The solution was extracted with 1M hydrochloric acid solution to remove triethylamine and form the free acid. The organic layer was dried with anhydrous magnesium sulfate, filtered over celite to remove any residual Ni/SiO$_2$ catalyst, and concentrated under reduced pressure. Water (10 mL) and concentrated sulfuric acid (10 to 20 mmol) was added to the crude dialkyl N-(phosphonomethyl)diacetic acid and the solution was heated to 85° C. Hydrogen peroxide (30 wt. %, 10 mL) was added dropwise over 1 hour. Stirring was continued at 85° C. for 4 to 6 hours. The solution was kept in the freezer overnight, where a white precipitate formed. Further precipitation of the product was facilitated using ethanol. The solid was identified as glyphosate by $^{31}$P-NMR analysis with a purity of 93%.

Detailed Experimental Section

The detailed experimental work which went into the reduction of the invention to practice will now be described in greater detail. As briefly discussed, based on their superior properties of solubility and considerably lower toxicity, Applicants have proposed phosphinates (hypophosphorous acid, HPA, and its derivatives) as the best practical alternative to PCl$_3$ for producing the organophosphorus compounds of interest. Additional support for phosphinates resides in their synthetic flexibility in terms of the wide range of accessible functionalities, and the fact that each phosphorus atom can be incorporated into products.

H-Phosphonate diesters (RO)$_2$P(O)H and phosphorous acid (R═H) constitute a major class of intermediates used in fine and industrial organophosphorus chemistry. They are currently prepared from the alcoholysis or hydrolysis of PCl$_3$, respectively (Scheme 1). Both the base (such as Et$_3$N) and chlorine can be recycled, but the process requires extensive manipulations Scheme 1. Preparation of H-phosphonate diesters.

a) Base-Promoted Process

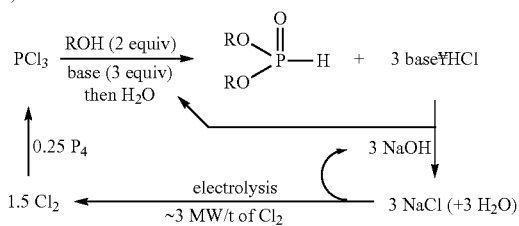

b) Base-Free Process

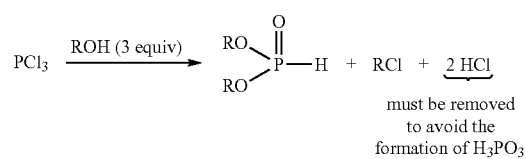

and electric power. The exception is phenol which does not require any base because PhCl cannot form.

Herein, Applicants describe the catalytic oxidative phosphorylation reaction of various alcohols with HPA to form H-phosphonate diesters in a simple, yet chlorine-free and base-free process (Scheme 2). The formation of hydrogen should be noted.

Scheme 2. H-phosphonate diester synthesis from HPA.

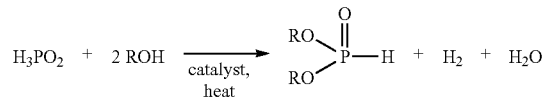

Results and Discussion

Applicants have previously reported the results of work involving catalytic phosphorus-oxygen bond formations: For example, with H$_3$PO$_2$ (1.5 equiv) and an alcohol (1 equiv) using either Pd/C or Ni/Al$_2$O$_3$/SiO$_2$ as catalysts, we were able to prepare H-phosphonate monoesters. These compounds are normally prepared from PCl$_3$ or a reagent derived from it. The work exploited the transfer hydrogenation pathway to prepare organophosphorus compounds via catalytic P—O bond formation. Until Applicants work, what happens to the hypophosphite in transfer hydrogenation was largely overlooked since the organic product was desired. However, Dorfman and Aleshkova reported in 1998 a seminal study of the oxidation of sodium hypophosphite by alcohols using palladium or nickel catalysts The reaction produces ROP(O)(ONa)H and an equivalent amount of hydrogen.

However, dialkyl H-phosphonates are much more important industrially than the monoesters because dialkyl phosphonates are ubiquitous. As has been discussed, the best illustration may be for the synthesis of N-phosphonomethyl glycine, the active component of the herbicide glyphosate. However, industrial preparations of glyphosate rely either on PCl$_3$ or its derivatives: phosphorous acid, or dialkyl H-phosphonates.

Alkyl phosphinates ROP(O)H$_2$ can be prepared in several ways from HPA.[11] The most general and inexpensive methods use alkoxysilanes, or the Dean-Stark method for higher boiling alcohols. It occurred to Applicants that alkyl phosphinates might be converted into symmetrical H-phosphonate diesters as long as excess alcohol ROH is available. In other words, more than the stoichiometric amount normally needed to complete the reaction. In the instant case, the stoichiometry requires ROP(O)H$_2$+ROH. Since Applicants are making ROP(O)H$_2$ with a silicate or an alcohol, it is only necessary to insure that enough reagent is present to accomplish this task. The stoichiometry then is, for example, H$_3$PO$_2$+2 BuOH gives (BuO)$_2$P(O)H.

Therefore, conditions that maximize transfer hydrogenation when both ROP(O)H$_2$ and excess ROH are combined could follow the mechanism shown in Scheme 3.

Scheme 3. Proposed mechanism for the metal-catalyzed formation of H-phosphonate diesters.

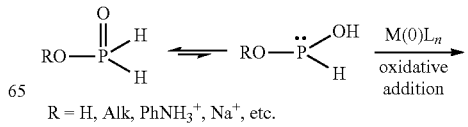

R = H, Alk, PhNH$_3^+$, Na$^+$, etc.

-continued

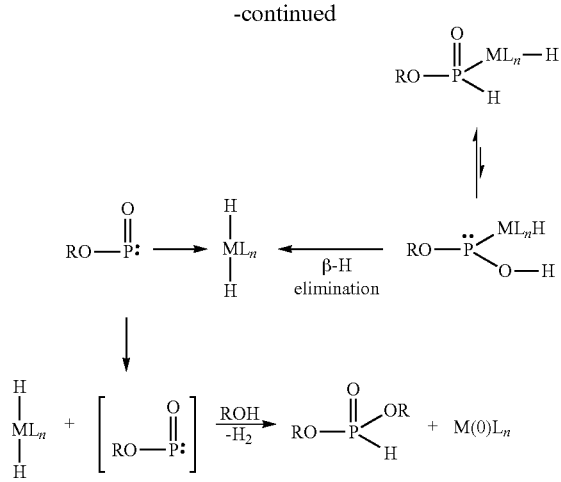

Scheme 3. Proposed mechanism for the metal-catalyzed formation of H-phosphonate diesters. Ligandless metals are expected to catalyze the transfer hydrogenation process through facile βhydrogen elimination. Also, because of their strong reducing properties, alkyl phosphinates are able to reduce metal salts easily. Scheme 4 summarizes the conditions that were investigated.

Scheme 4. Reaction conditions for Table 1.

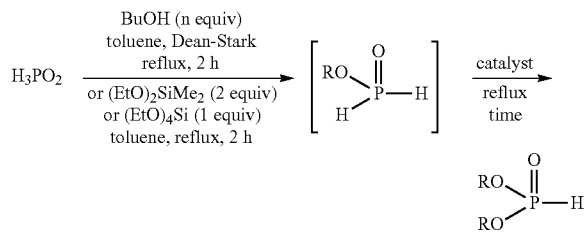

Table 1 shows the result of various experiments. First, a solution of EtOP(O)H$_2$ was treated with nickel chloride. Entries 1 and 2 show the influence of the amount of catalyst on the transformation. In order to avoid any additional silicate reagent, Applicants next focused on BuOP(O)H$_2$ prepared by the Dean-Stark reaction, since in this case, an excess alcohol could be used as the source of the second ester group. The decomposition of ROP(O)H$_2$ is well known but entry 3 shows that this uncatalyzed process is inefficient as a synthetic procedure. Addition of NiCl$_2$ results in a clean reaction with quantitative formation of (BuO)$_2$P(O)H. Entry 4 shows that the reaction is fast and that even inexpensive nickel chloride hexahydrate is an excellent catalyst.

Not surprisingly, other nickel(II) halides reacted satisfactorily (entries 6 and 7). On the other hand, nickel(II) acetate, acetylacetonate, and nickel powder gave poorer results. Because nickel on silica had given good results in the synthesis of H-phosphonate monoesters it was investigated next. This catalyst was clearly less efficient than NiCl$_2$ (entries 4 and 5) but increasing the reaction time gave clean reactions and high conversions (entry 15). It should be noted that adding the catalyst from the start of the reaction is unsatisfactory (entry 13). Using n-butanol as solvent instead of toluene also gave excellent results (entry 14 versus 15). This might be useful for easily recycling BuOH in an industrial process. In spite of lower activity, one advantage of Ni/SiO$_2$ over NiCl$_2$ is that it can be recycled (entry 16). Finally, palladium (entries 17-19) and copper catalysts (20-22) were investigated but did not offer better results.

TABLE 1

Conditions Optimization

| Entry | R | ROH (equiv) | Catalyst | Catalyst (mol-%) | Time (h) | $^{31}$P-NMR yield % (isolated yield)[a] |
|---|---|---|---|---|---|---|
| 1[b] | Et | 0 | NiCl$_2$ | 1.5 | 3 | 36 |
| 2[b] | Et | 0 | NiCl$_2$ | 3 | 3 | 95 |
| 3 | Bu | 2.5 | none | 0 | 18 | 17 |
| 4 | Bu | 3 | NiCl$_2$ | 3 | 3 | 95 |
| 5 | Bu | 2.5 | NiCl$_2$•6H$_2$O | 3 | 3 | 95 |
| 6 | Bu | 2.5 | NiBr$_2$ | 3 | 3 | 99 |
| 7 | Bu | 2.5 | NiI$_2$ | 3 | 3 | 95 |
| 8 | Bu | 2.5 | Ni(OAc)$_2$ | 3 | 3 | 51 |
| 9 | Bu | 2.5 | Ni(acac)$_2$ | 3 | 3 | 67 |
| 10 | Bu | 2.5 | Ni powder | 3 | 3 | 27 |
| 11[b,c] | Et | 0 | Ni/SiO$_2$ | 3 | 16 | 53 |
| 12 | Bu | 2.5 | Ni/SiO$_2$ | 3 | 3 | 55 |
| 13[d] | Bu | 2.5 | Ni/SiO$_2$ | 5 | 30 | 77 |
| 14 | Bu | solvent | Ni/SiO$_2$ | 5 | 18 | 100 (84) |
| 15 | Bu | 3 | Ni/SiO$_2$ | 5 | 18 | 100 (90) |
| 16[e] | Bu | 3 | Ni/SiO$_2$ | 5 | 18 | 100 (75) |
| 17 | Bu | 2.5 | Pd/C | 2 | 3 | 65 |
| 18 | Bu | 3 | Pd/C | 5 | 16 | 72 (71) |
| 19 | Bu | 2.5 | PdCl$_2$ | 3 | 3 | 78 |
| 20 | Bu | 2.5 | CuCl | 3 | 3 | 16 |
| 21 | Bu | 2.5 | CuCl$_2$ | 3 | 3 | 26 |
| 22 | Bu | 2.5 | Cu powder | 3 | 3 | 17 |

[a]NMR yields are determined by integration of all resonances in the $^{31}$P-NMR spectra. For isolation, see experimental details.
[b]Prepared by the alkoxysilane method.
[c]An extra equivalent of (EtO)$_2$SiMe$_2$ was added in the second step.
[d]Catalyst added at the start (before esterification).
[e]The catalyst from entry 14 was recycled and used for this experiment on a 25 mmol scale.

After the above investigation, the conclusion was that NiCl$_2$ was a superior catalyst to convert ROP(O)H$_2$ into (RO)$_2$P(O)H, but that because Ni/SiO$_2$ can be recycled, it provides a greener process. Next attention was turned to the scope of the reaction under conditions similar to those in Scheme 4. The results are shown in Table 2. For low boiling alcohols like ethanol, which cannot be conveniently esterified through azeotropic removal of water, the alkoxysilane method was used. Diethyl H-phosphonate could be made in good yield (entry 1). For diisopropyl H-phosphonate, the intermediate phosphinate was prepared using a Soxhlet extractor with 3 Å MS to remove water, and substituting cyclohexane for toluene to give the product in excellent yield (entry 2).

Overall, a wide range of primary and secondary alcohols could be transformed into the corresponding H-phosphonate diester (entries 3-10), and in a vast majority of examples chromatographic purification is completely avoided. In some cases isolation is difficult such as the H-phosphonate prepared from (−)-menthol which azeotropes off with the starting alcohol during distillation (entry 8). The product prepared from trichloroethanol is difficult to separate from the dechlorinated products formed during the reaction (entry 10). 1-Adamantanol did react in moderate yield (entry 11) thus supporting the intermediacy of a highly reactive phosphinidene oxide (Scheme 3). Other tertiary alcohols are problematic because of competing elimination in the esterification step. In the preparation of phosphorous acid (H$_3$PO$_3$), since HPA is a 50 wt.-% solution in water, which is the desired nucleophile, heating the solution in the presence of catalyst gives an excellent yield of product. Similar results were obtained with Ni/Al$_2$O$_3$ (71% isolated yield). In a control experiment without any catalyst, HPA remained unchanged. The case of sodium hypophosphite is interesting because unlike with HPA, over-oxidation to sodium dihydrogen phosphate is the dominant pathway in our hands (entry 13). Shortening the reaction time improves the yield significantly (entry 14), but still a large amount of phosphate is formed.

TABLE 2

Scope of the reaction.[a]

| Entry | R | Catalyst | $^{31}$P-NMR yield % (isolated yield)[b] |
|---|---|---|---|
| 1[c,d,e] | Et | Ni/SiO$_2$ | 92 (75) |
| 2[f] | iPr | Ni/SiO$_2$ | 100 (87) |
| 3 | iBu | Ni/SiO$_2$ | 100 (84) |
| 4[g] | nPent | Ni/SiO$_2$ | 100 (55) |
| 5 | Cy | Ni/SiO$_2$ | 100 (75) |
| 6 | Bn | Ni/SiO$_2$ | 68 (64) |
| 7 | PhCH$_2$CH$_2$ | Ni/SiO$_2$ | 100 (81) |
| 8 | (−)-Menthyl | Ni/SiO$_2$ | 100 (49) |
| 9 | Fenchyl | Ni/SiO$_2$ | 100 (82) |
| 10 | Cl$_3$CCH$_2$ | Ni/SiO$_2$ | 81 (26) |
| 11 | 1-Adamantyl | NiCl$_2$ | 68 (60) |
| 12[h] | H | Ni/SiO$_2$ | 100 (84) |
| 13[h] | Na | Ni/SiO$_2$ | 14[j] |
| 14[h,i] | Na | Ni/SiO$_2$ | 53[j] |

[a]Unless otherwise noted, the reactions were conducted with ROH (3 equiv), 5 mol-% of catalyst, for 18 h
[b]NMR yields are determined by integration of all resonances in the $^{31}$P-NMR spectra.. For isolation, see experimental details.
[c]Prepared by the alkoxysilane method.
[d]40 h.
[e]Anhydrous ethanol (3 equiv) was added in the second step.
[f]Cyclohexane was the solvent.
[g]87 h
[h]Water is the solvent.
[i]The balance is NaH$_2$PO$_4$.
[j]2 h.

Because HPA can be oxidized easily into H$_3$PO$_3$ an alternative approach to manufacturing glyphosate while by-passing PCl$_3$ is to use H$_3$PO$_3$, i.e., by oxidizing H$_3$PO$_2$ to H$_3$PO$_3$ and esterifying (RO)$_2$P(O)H via H$_3$PO$_3$. As mentioned earlier, glyphosate can be manufactured using H$_3$PO$_3$. In terms of H-phosphonate diesters, we briefly investigated the Dean-Stark esterification of H$_3$PO$_3$. In Applicants process, the intermediate H$_3$PO$_3$ does not need to be isolated since it is formed in quantitative yield (see Table 2, entry 12).

Although the conversion of HPA into H$_3$PO$_3$ is known, Applicants' method is mild even if the subsequent conversion of H$_3$PO$_3$ into (RO)$_2$P(O)H is limited, often only giving instead the monoester or a mixture of monoester and diester (Scheme 6).[19] Also, water can be the solvent.

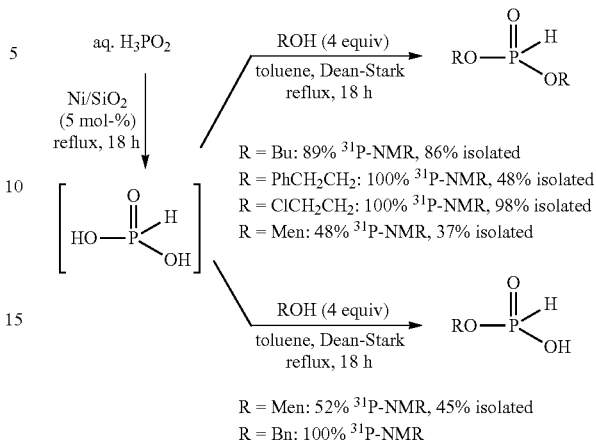

Scheme 6. One-pot conversion of HPA into (RO)$_2$P(O)H via H$_3$PO$_3$.

Nonetheless, 2-chloroethanol was an excellent substrate. The ease of oxidation of ClCH$_2$CH$_2$OP(O)H$_2$ would be due to a higher availability of its P(III) tautomer. The Dean-Stark esterification of H$_3$PO$_3$ with phenol is slow (3 days) but gives a mixture like in Table 2, entry 7, also suggesting that ROP(O)(OH)H might be an intermediate.

Conclusions and Advantages of the Invention

Esterification of hypophosphorous acid followed by reaction with another molecule of alcohol under the action of a nickel catalyst provides a green method for the preparation of H-phosphonates. This method entirely avoids the need for any stoichiometric chloride unlike those based on phosphorus trichloride.

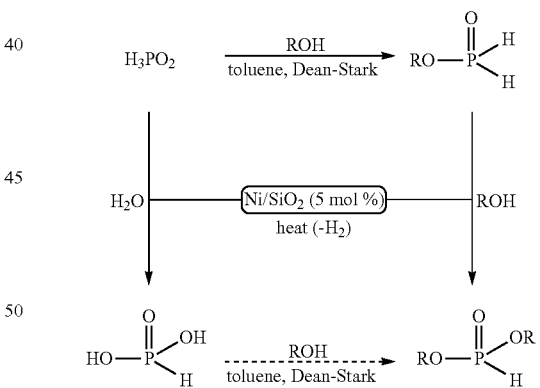

There are numerous literature methods to prepare H-phosphonate diesters, including transesterification. However to the best of Applicants knowledge, the present methodology is the only one that does not rely on PCl$_3$ at any point and is atom economical. The proposed reaction is greener than the alternative because, in its preferred form, it only uses H$_3$PO$_2$, an alcohol, and nickel on silica gel as a catalyst, which might perhaps be reused and no by-products (except hydrogen) are formed. Nickel chloride is a superior catalyst for this transformation, but it cannot be reused. The present reaction thus provides an important link between hypophosphorous chemistry and key intermediates that are normally prepared through PCl$_3$.

Thus, it is another tool in the growing methodological toolbox for a phosphorus economy based on hypophosphites. Also the reaction via ROP(O)H$_2$ appears much more general than the direct esterification of phosphorous acid. The process of the invention not only provides access to an important class of industrial intermediates, it also could provide valuable hydrogen instead of hydrogen chloride associated with the current use of PCl$_3$.

Procedures Used in the Experimental Section

General Procedure for the Nickel-Catalyzed Transformation of HPA into (RO)$_2$P(O)H:

(Table 1, entry 14). Aqueous H$_3$PO$_2$ (50 wt.-%, 25 mmol) was concentrated in vacuo for 15 min at r.t. [Note: this step can be omitted as long as the esterification time is monitored]. Butanol (3 equiv, 75 mmol) followed by toluene (reagent grade, 50 mL) was added to the flask, and a Dean-Stark trap filled with excess toluene was fitted on the flask. The reaction was heated to reflux for 2 h under nitrogen atmosphere. The solution was cooled and the yield of BuOP(O)H$_2$ was quantitative as determined by $^{31}$P-NMR. The Dean-Stark trap was removed, and Ni/SiO$_2$ (64 wt.-%, 5 mol-%) was added to the BuOP(O)H$_2$ solution. The solution was refluxed under nitrogen for 18 h. After cooling down, the reaction was filtered through Celite® and rinsed with ethyl acetate (20 mL). The organic layer was washed with brine (50 mL), and the aqueous layer was further extracted with ethyl acetate (3×15 mL). The combined organic layers was dried over MgSO$_4$ and concentrated in vacuo to afford dibutyl H-phosphonate as a light yellow liquid in 4.37 g (90% isolated yield). $^1$H NMR (300 MHz, CDCl$_3$) δ 6.83 (d, $^1J_{HP}$=691.9 Hz, 1H, H—P); 4.09 (q, $^3J$=7.46 Hz, 4H, CH$_2$); 1.70 (p, $^3J$=6.68 Hz, 2H, CH$_2$); 1.43 (p, $^3J$=7.25 Hz, 2H, CH$_2$); 0.96 (t, $^3J$=5.33 Hz, 6H, CH$_3$) $^{31}$P NMR (121.46 MHz, CDCl$_3$) δ 7.82 (dp, $^1J_{PH}$=693.23 Hz; $^3J_{POC}$=9.72 Hz).

Diethyl H-phosphonate: (Table 2, entry 1). Aqueous H$_3$PO$_2$ (50 wt.-%, 25 mmol) was concentrated in vacuo for 30 min at r.t. Octyltriethoxysilane (1 equiv, 25 mmol) and toluene (reagent grade, 50 mL) were added, and the reaction was heated to reflux for 3 h. After completion, the solution was cooled to r.t. and Ni/SiO$_2$ (64 wt.-%, 5 mol-%) and anhydrous ethanol (3 equiv, 75 mmol) were added. The reaction was heated to reflux and allowed to react under nitrogen for 40 h. After cooling down, the reaction was filtered through Celite® and was rinsed with ethyl acetate (20 mL). The organic layer was concentrated and subsequently dissolved in CH$_3$CN (HPLC grade, 50 mL). The CH$_3$CN layer was partitioned with hexanes (4×15 mL), and concentrated in vacuo to obtain a discolored liquid in 2.59 g (75% isolated yield). $^1$H NMR (400 MHz, CDCl$_3$) δ 6.82 (d, $^1J_{HP}$=692.8 Hz, 1H, H—P); 4.16 (p, $^3J$=7.20 Hz, 4H, CH$_2$); 1.37 (t, 6.80 Hz, 6H, CH$_3$) $^{31}$P NMR (161.97 MHz, CDCl$_3$) δ 7.77 (dm, $^1J_{PH}$=691.61 Hz).

Diisopropyl H-Phosphonate:

(Table 2, entry 2). Aqueous H$_3$PO$_2$ (50 wt.-%, 62.5 mmol) was concentrated in vacuo for 30 min at r.t. Isopropanol (7 equiv, 438 mmol) and cyclohexane (92 mL) were added and a soxhlet extractor was placed on the reaction flask with 3 Å molecular sieves placed inside the extraction thimble. The solution was refluxed for a total of 18 h with the molecular sieves replaced after 4 and 8 hours. Ni/SiO$_2$ (64 wt.-%, 5 mol %) was added to the iPrOP(O)H$_2$ solution (25 mmol, 50 mL) and heated to reflux for 18 h under nitrogen. The cooled solution was filtered through Celite® and concentrated in vacuo to obtain a clear liquid in 4.15 g (87% isolated yield). $^1$H NMR (400 MHz, CDCl$_3$) δ 6.85 (d, $^1J_{HP}$=687.60 Hz, 1H, H—P); 4.74 (m, 2H, CH); 1.36 (d, $^3J$=8.40 Hz, 12H, CH$_3$) $^{31}$P NMR (161.97 MHz, CDCl$_3$) δ 4.45 (dt, $^1J_{PH}$=686.75 Hz; $^3J_{POC}$=8.10 Hz).

Diisobutyl H-Phosphonate:

(Table 2, entry 3). After concentration, 4.08 g (84%) light yellow liquid was obtained. $^1$H NMR (300 MHz, CDCl$_3$) δ 6.83 (d, $^1J_{HP}$=692.7 Hz, 1H), 3.88-3.82 (m, 4H), 1.97 (m, 1H), 0.97 (d, 6H, $^3J$=6.9 Hz); $^{31}$P NMR (121.46 MHz, CDCl$_3$) δ 7.99 (d, $^1J_{PH}$=693 Hz, $^3J_{POC}$=7.76 Hz).

Dineopentyl H-Phosphonate:

(Table 2, entry 4). After Kugelrohr distillation of excess alcohol, 3.06 g (55%) of light yellow liquid was obtained. $^1$H NMR (400 MHz, CDCl$_3$) δ 6.85 (d, $^1J_{HP}$=693.6 Hz, 1H); 3.77-3.73 (p, 4H, $^3J$=6.8 Hz), 0.98 (s, 18H); $^{31}$P NMR (CDCl$_3$, 161.97 Hz) δ 8.38 (d, $^1J_{PH}$=695 Hz, $^3J_{POC}$=8.10 Hz).

Dicyclohexyl H-Phosphonate:

(Table 2, entry 5). After Kugelrohr distillation of excess alcohol, 6.16 g (75%) clear liquid was obtained. $^1$H NMR (400 MHz, CDCl$_3$) δ 6.89 (d, $^1J_{HP}$=688.4 Hz, 1H), 4.46-4.44 (m, 2H), 1.96-1.93 (m, 4H), 1.78-1.74 (m, 4H), 1.58-1.53 (m, 6H), 1.37-1.1.30 (m, 6H); $^{31}$P NMR (161.97 MHz, CDCl$_3$) δ 4.46 (d, $^1J_{PH}$=688 Hz).

Dibenzyl H-Phosphonate:

(Table 2, entry 6). After Kugelrohr distillation of excess alcohol, 4.20 g (64%) of light yellow liquid was obtained. $^1$H NMR (400 MHz, CDCl$_3$) δ 7.39-7.37 (m, 10H, ArCH), 6.97 (d, $^1J_{HP}$=706.8 Hz, 1H, H—P), 5.08 (m, 4H, CH$_2$); $^{31}$P NMR (161.97 MHz, CDCl$_3$) δ 7.74 (dp, $^1J_{PH}$=706 Hz, $^3J_{POC}$=9.3 Hz).

Bis(2-phenethyl) H-phosphonate:

(Table 2, entry 7). After Kugelrohr distillation of excess alcohol, 7.26 g (81%) of light yellow liquid was obtained. $^1$H NMR (400 MHz, CDCl$_3$) δ 7.33-7.23 (m, 10H), 6.66 (d, $^1J_{HP}$=700.8 Hz, 1H), 4.24-4.20 (m, 4H); $^{31}$P NMR (161.97 MHz, CDCl$_3$) δ 7.65 (dp, $^1J_{PH}$=700 Hz, $^3J_{POC}$=8.10 Hz).

Dimenthyl H-phosphonate:

(Table 2, entry 8). After Kugelrohr distillation, 4.39 g (49%) of clear liquid was obtained. $^1$H NMR (400 MHz, CDCl$_3$) δ 6.91 (d, 1H, $^1J_{HP}$=686.8 Hz), 4.28-4.18 (m, 2H), 2.20-2.16 (m, 2H), 2.15-2.04 (2×m, 2H), 1.69, 1.65 (2×s-br), 1.47-1.44 (m, 2H), 1.26-1.16 (m, 2H), 1.07-0.96 (m, 4H), 0.92 (2×d, 12H, $^3J$=1.32 Hz, $^3J$=1.68 Hz), 0.89-0.84 (m, 2H), 0.82 (d, 3H, $^3J$=1.68 Hz), 0.79 (d, 3H, $^3J$=1.68 Hz); $^{31}$P NMR (161.97 MHz, CDCl$_3$) δ 5.45 (dt, $^1J_{PH}$=686.8 Hz, $^3J_{POC}$=8.73 Hz).

Difenchyl H-Phosphonate:

(Table 2, entry 9). After Kugelrohr distillation of excess alcohol, 7.27 g (82%) of light brown liquid was obtained. $^1$H NMR (400 MHz, CDCl$_3$) δ 6.89 (d, $^1J_{HP}$=686.4 Hz, 1H), 4.06-3.98 (m, 2H), 1.74-1.70 (m, 6H), 1.56-1.53 (m, 2H), 1.49-1.44 (m, 2H), 1.23-1.20 (m, 2H), 1.14 (d, 6H, $^3J$=8.6 Hz), 1.09 (m, 8H), 0.96 (s, 3H), 0.94 (s, 3H); $^{13}$C NMR (100.62 MHz, CDCl$_3$) δ 89.3 (d, $^2J_{COP}$=7.3 Hz), 49.1, 40.9, 39.5, 29.8, 25.8, 21.4, 19.3; $^{31}$P NMR (161.97 MHz, CDCl$_3$) δ 8.12 (dt, $^1J_{PH}$=688.4 Hz, $^3J_{POC}$=10.6 Hz); HRMS (ESI) calcd. for C$_{20}$H$_{35}$O$_3$P ([M+H]$^+$) 355.2402. found 355.2489.

Bis(2,2,2-trichloroethyl) H-phosphonate:

(Table 2, entry 10). After Kugelrohr distillation of excess alcohol and column chromatography, 2.24 g (26%) of light yellow liquid was obtained. $^1$H NMR (400 MHz, CDCl$_3$) δ 7.22 (d, $^1J_{HP}$=746 Hz, 1H), 4.75-4.66 (m, 4H); $^{31}$P NMR (161.97 MHz, CDCl$_3$) δ 7.23 (dp, $^1J_{PH}$=753 Hz, $^3J_{POC}$=8.75 Hz).

Diadamantyl H-Phosphonate:

(Table 2, entry 11). After Kugelrohr distillation of excess alcohol, 5.61 g (64%) of white solid was obtained. $^1$H NMR (400 MHz, CDCl$_3$) δ 7.04 (d, $^1J_{HP}$=680 Hz, 1H), 2.18 (m, 6H), 2.10 (m, 12H), 1.63 (m, 12H); $^{13}$C NMR (100.62 MHz, CDCl$_3$) 82.3 (d, $^2J_{COP}$=7.62 Hz), 44.0 (d, $^3J_{CCOP}$=4.51 Hz), 35.7, 31.0; $^{31}$P NMR (161.97 MHz, CDCl$_3$) δ −4.06 (d, $^1J_{PH}$=680 Hz); HRMS (ESI) calcd. for C$_{20}$H$_{31}$O$_3$P ([M+H]$^+$) 351.2089. found 351.2104.

Phosphorous Acid:

(Table 2, entry 12). After concentration of water, 1.72 g (84%) of clear liquid was obtained. $^1$H NMR (400 MHz, CDCl$_3$) δ 6.72 (d, $^1J_{HP}$=663.2 Hz, 1H); $^{31}$P NMR (161.97 MHz, CDCl$_3$) δ 4.37 (d, $J_{PH}$=664 Hz).

Dibutynyl H-Phosphonate:

(Table 2, entry 15). After Kugelrohr distillation of excess alcohol, 2.37 g (51%) of clear liquid was obtained. $^1$H NMR (400 MHz, CDCl$_3$) δ 6.95 (d, $^1J_{HP}$=711 Hz, 1H), 4.28-4.17 (m, 4H), 2.65-2.61 (td, $^3J$=6.68 Hz, $^4J$=2.64 Hz), 2.07 (t, $^4J$=2.64 Hz); $^{13}$C NMR (100.62 MHz, CDCl$_3$) δ 79.3, 70.7, 63.5 (d, $^2J_{COP}$=6.01 Hz), 20.9 (d, $^3J_{CCOP}$=6.26 Hz) $^{31}$P NMR (161.97 MHz, CDCl$_3$) δ 7.74 (dp, $^1J_{PH}$=712 Hz, $^3J_{POC}$=9.72 Hz); HRMS (ESI) calcd. for C$_8$H$_{11}$O$_3$P ([M+H]$^+$), 187.0524. found 187.0570.

Bis(2-chloroethyl)H-phosphonate:

(Table 2, entry 16). After Kugelrohr distillation of excess alcohol, 5.17 g (68%) of clear liquid was obtained. $^1$H NMR (400 MHz, CDCl$_3$) δ 7.02 (d, $^1J_{HP}$=720.8 Hz, 1H), 4.40-4.33 (m, 4H), 3.76-3.71 (t, 4H, $^3J$=8.4 Hz); $^{31}$P NMR (161.97 MHz, CDCl$_3$) δ 8.18 (dp, $^1J_{PH}$=720 Hz, $^3J_{POC}$=8.9 Hz).

Diphenyl H-Phosphonate:

(Table 2, entry 17). After Kugelrohr distillation of excess alcohol, 3.69 g (63%) of light yellow liquid was obtained. $^1$H NMR (400 MHz, CDCl$_3$) δ 7.41-7.22 (m, 10H), 7.34 (d, $^1J_{HP}$=728.4 Hz, 1H); $^{31}$P NMR (161.97 MHz, CDCl$_3$) δ 0.34 (d, $^1J_{PH}$=733 Hz).

Preparation of Dibutyl H-Phosphonate from Phosphorous Acid:

(Scheme 6). Ni/SiO$_2$ (64 wt.-%, 5 mol-%) was added to a round-bottom flask containing aqueous H$_3$PO$_2$ (50 wt.-%, 25 mmol), and the mixture was heated to reflux for 18 h under nitrogen. [Note: if the reaction is conducted open to air, the reaction time is lowered to 6 h.] Once cooled, $^{31}$P-NMR analysis showed that the formation of phosphorous acid was complete. The solution was filtered through Celite® and rinsed with several aliquots of deionized water (~20 mL total). The acid was concentrated, and butanol (4 equiv, 100 mmol) and toluene (reagent grade, 50 mL) were added. A Dean-Stark trap pre-filled with toluene was place on the reaction vessel and the solution was heated to reflux for 18 h under nitrogen. After cooling, the solution was extracted with brine (50 mL), dried over MgSO$_4$ and concentrated in vacuo to afford a light yellow liquid in 4.18 g (86%) isolated yield.

While the invention has been described in only one of its forms, it is not thus limited, but is susceptible to various changes and modifications without departing from the spirit thereof.

What is claimed is:

1. A method for producing H-phosphonates circumventing the use of chlorine, the method comprising the steps of:
   reacting hypophosphorous acid with an alcohol to produce a phosphinate and an excess of alcohol;
   reacting the phosphinate in the presence of the excess alcohol with a metal catalyst to produce an H-phosphonate.

2. The method of claim 1, wherein the H-phosphonate so produced has the structural formula:

(RO)$_2$P(O)H where R=alkali metal, hydrogen, alkyl, aryl.

3. The method of claim 1, wherein the metal catalyst is selected from the group consisting of nickel, copper and palladium compounds and nickel on alumina.

4. The method of claim 2, wherein the metal catalyst is selected from the group consisting of NiCl$_2$ and Ni/SiO$_2$.

5. A method for producing H-phosphonates circumventing the use of chlorine, the method comprising the steps of:
   esterfying hypophosphorous acid by reacting the hypophosphorous acid with an alcohol to produce a phosphinate and an excess of alcohol;
   reacting the phosphinate with another molecule of alcohol under the action of a nickel catalyst to produce an H-phosphonate diester.

6. The method of claim 5, wherein the metal catalyst is selected from the group consisting of NiCl$_2$ and Ni/SiO$_2$.

7. The method of claim 5, wherein the step of reacting the phosphinate with another molecule of alcohol under the action of a nickel catalyst to produce an H-phosphonate diester occurs after the step of initially reacting the hypophosphorous acid with and alcohol has been allowed to proceed to esterfication.

8. A method for producing glyphosate circumventing the use of chlorine, the method comprising the steps of:
   esterfying hypophosphorous acid by reacting the hypophosphorous acid with an alcohol to produce a phosphinate and an excess of alcohol;
   reacting the phosphinate with another molecule of alcohol under the action of a nickel catalyst to produce an H-phosphonate diester;
   converting the H-phosphonate diester so produced to glyphosate.

9. The method of claim 8, wherein the nickel catalyst is selected from the group consisting of NiCl$_2$ and Ni/SiO$_2$.

10. The method of claim 8, wherein the method is carried out according to the following synthesis:

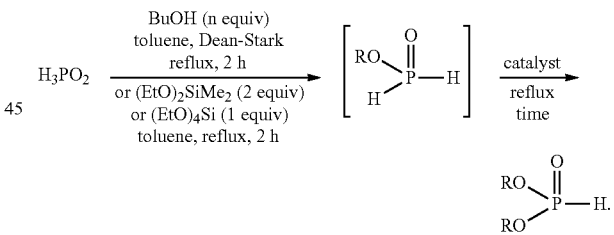

11. A method for producing H-phosphonates circumventing the use of chlorine, the method comprising the steps of:
    oxidizing hypophosphorous acid in the presence of a nickel catalyst to produce phosphorous acid using water as a solvent;
    or reacting hypophosphorous acid with excess alcohol in the presence of the nickel catalyst to produce an H-phosphonate.

12. The method of claim 11, wherein the nickel catalyst is selected from the group consisting of NiCl$_2$ and Ni/SiO$_2$.

* * * * *